United States Patent
Park et al.

(10) Patent No.: US 10,479,816 B2
(45) Date of Patent: Nov. 19, 2019

(54) DECOY PEPTIDES INHIBITING PROTEIN PHOSPHATASE 1-MEDICATED DEPHOSPHORYLATION OF PHOSPHOLAMBAN

(71) Applicant: BethphaGen Inc., Gwangju (KR)

(72) Inventors: Woo Jin Park, Gwangju (KR); Roger J. Hajjar, New York, NY (US); Jae Gyun Oh, Gwangju (KR)

(73) Assignee: BETHPHAGEN INC., Gwangju (KR)

( * ) Notice: Subject to any disclaimer, the term of this patent is extended or adjusted under 35 U.S.C. 154(b) by 0 days.

(21) Appl. No.: 16/224,438

(22) Filed: Dec. 18, 2018

(65) Prior Publication Data

US 2019/0112338 A1    Apr. 18, 2019

Related U.S. Application Data

(62) Division of application No. 14/413,005, filed as application No. PCT/KR2013/006009 on Jul. 5, 2013, now Pat. No. 10,208,085.

(60) Provisional application No. 61/668,034, filed on Jul. 5, 2012.

(51) Int. Cl.
| C07K 7/06 | (2006.01) |
| C07K 14/00 | (2006.01) |
| C07K 14/47 | (2006.01) |
| A61K 38/00 | (2006.01) |
| C07K 7/00 | (2006.01) |
| A61K 38/08 | (2019.01) |

(52) U.S. Cl.
CPC .............. *C07K 7/06* (2013.01); *A61K 38/005* (2013.01); *A61K 38/08* (2013.01); *C07K 7/00* (2013.01); *C07K 14/00* (2013.01); *C07K 14/47* (2013.01); *C07K 14/4703* (2013.01)

(58) Field of Classification Search
CPC ...... A61K 38/005; A61K 38/08; C07K 14/00; C07K 14/47; C07K 14/4703; C07K 7/00; C07K 7/06
See application file for complete search history.

(56) References Cited

U.S. PATENT DOCUMENTS

| 2004/0121942 A1 | 6/2004 | Chien et al. |
| 2004/0214760 A1 | 10/2004 | Gupta et al. |
| 2009/0203596 A1 | 8/2009 | Kranias et al. |
| 2010/0273212 A1 | 10/2010 | Reed et al. |

FOREIGN PATENT DOCUMENTS

| JP | 2010-0525824 A | 7/2010 |
| WO | WO-0025804 A2 | 5/2000 |

OTHER PUBLICATIONS

Chu G, Phospholamban as a therapeutic modality in heart failure, Novartis Found Symp. 2006;274:156-71; discussion 172-5, 272-6.*
Eto, Masumi, "Regulation of cellular protein phosphatase-1 (PP1) by phosphorylation of the CPI-17 family, C-kinase-activated PP1 inhibitors.", *The Journal of Biological Chemistry*, 2009, vol. 284, No. 51, pp. 35273-35277.
International Search Report for PCT/KR2013/006009, dated Oct. 18, 2013.
Invitation pursuant to Article 94(3) and Rule 71(1) EPC dated Oct. 31, 2016 in European Patent Application No. 13812631.3.
Karczewski, P., et al., "Site-specific phosphorylation of a phospholamban peptide by cyclic nucleotide- and Ca2+/calmodulin-dependent protein kinases of cardiac sarcoplasmic reticulum.", *Basic Research in Cardiology*, 1997, vol. 92, Suppl. 1, 37-43.
Leggatt, et al., (1997) "Cytotoxic T lymphocyte (CTL) adherence assay (CAA): a no-nradioactive assay for murine CTL recognition of peptide-MHC class I complexes." *Journal of Immunological Methods*, 201:1-10, Feb. 14, 1997.
Lockamy, E. L. et al., "Functional and physical competition between phospholamban and its mutants provides insight into the molecular mechanism of gene therapy for heart failure.", *Biochemical and Biophysical Research Communications*, 388-392.
NCBI, GenBank accession No. XP_002918542.1 (Jul. 29, 2010).
Oh, Jae Gyun et al., "Decoy peptides targeted to protein phosphatase 1 inhibit dephosphorylation of phospholamban in cardiomyocytes.", *Journal of Malecular and Cellular Cardiology*, Dec. 19, 2012, vol. 56, pp. 63-71.
Quirk, P.G., et al., (1996) "Conformational effects of serine phosphorylation in phospholamban peptides". *Eur. J. Biochem.* 236:85-91.
Uniprot Protein Database, Protein Accession AOA1V3YY38, DUF4440 domain containing protein, accessed on Jul. 3, 2017.

(Continued)

*Primary Examiner* — Rachael E Bredefeld
*Assistant Examiner* — Erinne R Dabkowski
(74) *Attorney, Agent, or Firm* — Harness, Dickey & Pierce, P.L.C.

(57) ABSTRACT

The present invention relates to decoy peptide or polypeptide consisting of a peptide sequence represented by the following Formula I: $X_1$-Ala-$X_2$-$X_3$-Ile-Glu-$X_4$ (I). It is noteworthy that the decoy peptide or polypeptide of the present invention significantly elevates phosphorylation levels of PLB by inhibiting PP1-mediated dephosphorylation. In addition, the decoy peptide or polypeptide provides cardio-protective effects by restoring of SERCA2a activity and inotropic effect of enhancing myocardial contractility. The present invention will contribute greatly to the prevention or treatment of diseases associated with PLB.

5 Claims, 8 Drawing Sheets
Specification includes a Sequence Listing.

(56) References Cited

OTHER PUBLICATIONS

Uniprot Protein Database, Protein Accession V4XQL6, putative acyltransferase, accessed on Jul. 3, 2017.
Office Action, Non-final Rejection, dated Jul. 27, 2017, in U.S. Appl. No. 14/413,005.
Office Action, Non-final Rejection, dated Jun. 15, 2018, in U.S. Appl. No. 14/413,005.
Office Action, Non-final Rejection, dated Feb. 6, 2018, in U.S. Appl. No. 14/413,005.

* cited by examiner

SEQUENCE LISTING

<160> NUMBER OF SEQ ID NOS: 11

<210> SEQ ID NO 1
<211> LENGTH: 9
<212> TYPE: PRT
<213> ORGANISM: Artificial Sequence
<220> FEATURE:
<223> OTHER INFORMATION: Decoy peptide psi.PLB-SE

<400> SEQUENCE: 1

Arg Ala Glu Thr Ile Glu Met Pro Gln
1               5

<210> SEQ ID NO 2
<211> LENGTH: 9
<212> TYPE: PRT
<213> ORGANISM: Artificial Sequence
<220> FEATURE:
<223> OTHER INFORMATION: Decoy peptide psi.PLB-TE

<400> SEQUENCE: 2

Arg Ala Ser Glu Ile Glu Met Pro Gln
1               5

<210> SEQ ID NO 3
<211> LENGTH: 9
<212> TYPE: PRT
<213> ORGANISM: Artificial Sequence
<220> FEATURE:
<223> OTHER INFORMATION: Decoy peptide psi.PLB-SD

<400> SEQUENCE: 3

Arg Ala Asp Thr Ile Glu Met Pro Gln
1               5

<210> SEQ ID NO 4
<211> LENGTH: 8
<212> TYPE: PRT
<213> ORGANISM: Artificial Sequence
<220> FEATURE:
<223> OTHER INFORMATION: Decoy peptide psi.PLB-8-mer

<400> SEQUENCE: 4

Ala Glu Thr Ile Glu Met Pro Gln
1               5

<210> SEQ ID NO 5
<211> LENGTH: 7
<212> TYPE: PRT
<213> ORGANISM: Artificial Sequence
<220> FEATURE:
<223> OTHER INFORMATION: Decoy peptide psi.PLB--7-mer

<400> SEQUENCE: 5

Arg Ala Glu Thr Ile Glu Met
1               5

<210> SEQ ID NO 6
<211> LENGTH: 6
<212> TYPE: PRT
<213> ORGANISM: Artificial Sequence
<220> FEATURE:
<223> OTHER INFORMATION: Decoy peptide psi.PLB-6-mer

<400> SEQUENCE: 6

Arg Ala Glu Thr Ile Glu
1               5

<210> SEQ ID NO 7
<211> LENGTH: 5
<212> TYPE: PRT
<213> ORGANISM: Artificial Sequence
<220> FEATURE:
<223> OTHER INFORMATION: Decoy peptide psi.PLB-5-mer

<400> SEQUENCE: 7

Arg Ala Glu Thr Ile
1               5

<210> SEQ ID NO 8
<211> LENGTH: 9
<212> TYPE: PRT
<213> ORGANISM: Artificial Sequence
<220> FEATURE:
<223> OTHER INFORMATION: Decoy peptide psi.PLB-wt

<400> SEQUENCE: 8

Arg Ala Ser Thr Ile Glu Met Pro Gln
1               5

<210> SEQ ID NO 9
<211> LENGTH: 5
<212> TYPE: PRT
<213> ORGANISM: Artificial Sequence
<220> FEATURE:
<223> OTHER INFORMATION: Minimal consensus sequence necessary for
      elevating PLB phosphorylation levels

<400> SEQUENCE: 9

Ala Ser Thr Ile Glu
1               5

<210> SEQ ID NO 10
<211> LENGTH: 52
<212> TYPE: PRT
<213> ORGANISM: Homo sapiens

<400> SEQUENCE: 10

Met Glu Lys Val Gln Tyr Leu Thr Arg Ser Ala Ile Arg Arg Ala Ser
1               5                   10                  15

Thr Ile Glu Met Pro Gln Gln Ala Arg Gln Lys Leu Gln Asn Leu Phe
            20                  25                  30

Ile Asn Phe Cys Leu Ile Leu Ile Cys Leu Leu Leu Ile Cys Ile Ile
        35                  40                  45

Val Met Leu Leu
    50

<210> SEQ ID NO 11
<211> LENGTH: 11
<212> TYPE: PRT
<213> ORGANISM: Human immunodeficiency virus

<400> SEQUENCE: 11

Tyr Gly Arg Lys Lys Arg Arg Gln Arg Arg Arg
1               5                   10

DECOY PEPTIDES INHIBITING PROTEIN PHOSPHATASE 1-MEDICATED DEPHOSPHORYLATION OF PHOSPHOLAMBAN

CROSS-REFERENCE TO RELATED APPLICATIONS

This application is a divisional application of U.S. patent application Ser. No. 14/413,005, filed 5 Jan. 2015, which is a national phase application of PCT Application No. PCT/KR2013/006009, filed on Jul. 5, 2013, which claims the benefit and priority of U.S. Provisional Patent Application No. 61/668,034, filed on Jul. 5, 2012. The entire disclosures of the applications identified in this paragraph are incorporated herein by reference.

STATEMENT AS TO FEDERALLY FUNDED RESEARCH

This invention was supported by the Global Research Laboratory Program (M6-0605-00-0001) funded by the Korean Government (MEST), a grant from the Systems Biology Infrastructure Establishment Grant provided by GIST, and NIH grant (HL-080498-01).

BACKGROUND OF THE INVENTION

Field of the Invention

The present invention relates to a decoy peptide or polypeptide of phospholamban capable of inhibiting the protein phosphatase 1-mediated dephosphorylation of phospholamban and its use as well as a method for preparing the decoy peptide or polypeptide.

Description of the Related Art

Heart failure remains a leading cause of mortality and morbidity worldwide [1-3]. It is characterized by an increased ventricular chamber size and reduced systolic function of the heart. Previous studies support the notion that abnormalities in cardiac contractility cause the initiation and progression of heart failure [4-6]. The contractility of cardiomyocytes is directly regulated by intracellular $Ca^{2+}$ cycling [7, 8]. A small amount of extracellular $Ca^{2+}$ enters cardiomyocytes through the voltage-dependent L-type $Ca^{2+}$ channel and is then followed by a large release of $Ca^{2+}$ from the sarcoplasmic reticulum (SR) through the ryanodine receptor (RyR) [9]. This increase in intracellular $Ca^{2+}$ triggers contraction of the myofilaments. Re-uptake of $Ca^{2+}$ back into the SR through the SR $Ca^{2+}$-ATPase (SERCA) 2a and the $Na^+/Ca^{2+}$ exchanger at the sarcolemma then initiates relaxation of the myofilaments.

Previous studies showed that decreased SERCA2a expression and activity are associated with heart failure in humans and animal models [10-12]. Therefore, the restoration of SERCA2a levels by increasing the gene dosage was thought to be a rational approach for the treatment of heart failure. This proved to be the case when using heart failure models of rats [13-15] and pigs [16]. Furthermore, adeno-associated virus-mediated delivery of SERCA2a was recently shown to be a safe and effective modality for improving the cardiac functions in heart failure patients [17, 18].

The activity of SERCA2a is negatively regulated by an endogenous inhibitor, PLB (phospholamban), which in turn is regulated by PKA (protein kinase A), CaMKII ($Ca^{2+}$/calmodulin-dependent protein kinase II), and PP1 (protein phosphatase 1). Phosphorylation at $Ser^{16}$ and $Thr^{17}$ of PLB by PKA and CaMKII, respectively, causes the disassociation of PLB from SERCA2a, permitting near-maximal $Ca^{2+}$-ATPase activity of SERC2a [19-21]. On the contrary, dephosphorylation of PLB at $Ser^{16}$ or $Thr^{17}$ by PP1 enhances the association between PLB and SERCA2a and the inhibition of SERCA2a by PLB [22, 23]. Intriguingly, reduced PLB phosphorylation [24-26] concomitantly with an increased PP1 activity [27, 28] has been observed in animal models and end-stage human heart failure. Therefore, normalization of PP1 activity and PLB phosphorylation would be a reasonable approach to enhance cardiac function and suppress the progression of heart failure.

Molecular decoys such as small peptides that mimic target proteins have been successfully utilized to interfere with protein-protein interactions [29], phosphorylation of target proteins by protein kinases [30], and dephosphorylation of phosphorylated proteins by phosphatases [31, 32].

Throughout this application, various patents and publications are referenced, and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to a decoy peptide or polypeptide for treating diseases associated with PBL, in particular, caused by decreased SERCA2a activity by dephosphorylation levels of PLB. As a result, we have synthesized a decoy peptide which significantly elevates phosphorylation levels of PLB. In addition, we have discovered that the decoy peptide increases contractile parameters in vitro and improves left ventricular developed pressure ex vivo. That is to say, we have found out that the decoy peptide or polypeptide provides cardio-protective effects by restoring of SERCA2a activity and inotropic effect of enhancing myocardial contractility and thus the decoy peptide or polypeptide would be used to treat the diseases associated with PLB by inhibiting dephosphorylation of PLB.

Accordingly, it is an object of this invention to provide a decoy peptide or polypeptide inhibiting PP1-mediated dephosphorylation of PLB by a competitive inhibition.

It is another object of this invention to provide a pharmaceutical composition for preventing or treating diseases associated with PLB.

It is still another object of this invention to provide a method for preparing the decoy peptide or polypeptide of PLB capable of inhibiting PP1-mediated dephosphorylation of PLB by a competitive inhibition.

It is further object of this invention to provide a method for preventing or treating diseases associated with PLB.

Other objects and advantages of the present invention will become apparent from the detailed description to follow taken in conjugation with the appended claims and drawings.

BRIEF DESCRIPTION OF THE DRAWINGS

FIGS. 2a and 2b show contractile parameters. Peak cell shortening, percentage of shortened cell length; –dL/dt, maximal rate of cell shortening; +dL/dt, maximal rate of cell relengthening. FIGS. 2c and 2d show average parameters of the transient $Ca^{2+}$ properties determined with Fura2/AM. Baseline $[Ca^{2+}]_i$, baseline intracellular $Ca^{2+}$ levels; $\Delta[Ca^{2+}]_i$ (340/380), increase in intracellular $Ca^{2+}$ levels in response to electric stimuli; τ (ms), $Ca^{2+}$ transient decay rate. Approximately 500 cells were chosen for the contractility and $Ca^{2+}$ transient measurements were taken from eight individual hearts. #, $P<0.05$; *, $P<0.01$ compared to control; error bars represent SD.

FIG. 3a shows rat hearts which were Langendorff-perfused, and subjected to 20 min of no-flow to induce global ischemia, and then followed by 30 min of reperfusion with co-administration of 1 μM TAT or ψpPLB-SE. The changes in left ventricular developed pressure (LVDP) are shown. n=4. *, $P<0.01$ compared to TAT; error bars represent SEM. FIG. 3b shows protein lysates which were prepared following reperfusion. Western blots probed with antibodies against phospho-PLB ($S^{16}$), phosphor-PLB ($T^{17}$), total PLB, Caspase 3, or GAPDH are shown.

DETAILED DESCRIPTION OF THIS INVENTION

Figure 1A:
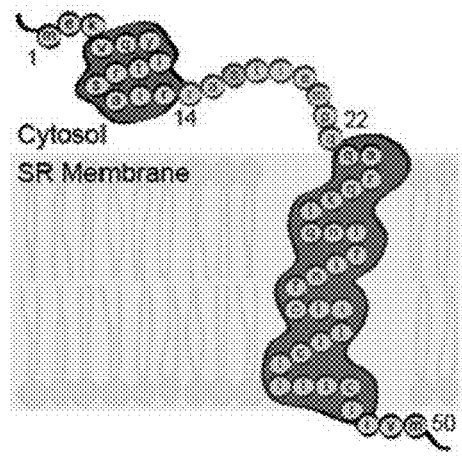
FIG. 1A represents the structure of monomeric PLB (left) and the amino acid sequences of decoy peptides (right); the "L-shaped" structure of monomeric PLB is composed of cytoplasmic helix, a connecting short loop, and a transmembrane helix. Peptides were derived from the nine amino acids that compose the connecting loop. In decoy peptides, Ser (S, serine) or Thr (T, threonine) residues were replaced with Glu (E, glutamic acid) to mimic phosphorylation. The replaced glutamic acid residues are underlined. TAT (SEQ ID NO:11); RASTIEMPQ (SEQ ID NO:8); RAETIEMPQ (SEQ ID NO:1); RASEIEMPQ (SEQ ID NO:2).

In one aspect of this invention, there is provided a decoy peptide or polypeptide consisting of a peptide sequence represented by the following Formula I:

$$X_1\text{-Ala-}X_2\text{-}X_3\text{-Ile-Glu-}X_4 \quad (I)$$

wherein $X_1$ represents 0-50 amino acid residue(s), $X_2$ represents Ser, Glu, or Asp, $X_3$ represents Thr, Glu, or Asp and $X_4$ represents 0-50 amino acid residue(s), with the proviso that $X_2$ is not Ser when $X_3$ is Thr; wherein the decoy peptide or polypeptide inhibits the PP1-mediated dephosphorylation of PLB by a competitive inhibition.

The present inventors have made intensive researches to a decoy peptide or polypeptide for treating diseases associated with PBL, in particular, caused by decreased SERCA2a activity by dephosphorylation levels of PLB. As a result, we have synthesized a decoy peptide which significantly elevates phosphorylation levels of PLB. In addition, we have discovered that the decoy peptide increases contractile parameters in vitro and improves left ventricular developed pressure ex vivo. That is to say, we have found out that the decoy peptide or polypeptide provides cardio-protective effects by restoring of SERCA2a activity and inotropic effect of enhancing myocardial contractility and thus the decoy peptide or polypeptide would be used to treat the diseases associated with PLB by inhibiting dephosphorylation of PLB.

The decoy peptide or polypeptide of the present invention consisting of a peptide sequence represented by the following Formula I: $X_1$-Ala-$X_2$-$X_3$-Ile-Glu-$X_4$ (I).

The decoy peptide or polypeptide designed to mimic phosphorylated PLB inhibits PP1-mediated dephosphorylation of PLB and significantly elevates phosphorylation levels of PLB and increases contractile parameters, thereby significantly improving left ventricular developed pressure. The decoy peptide or polypeptide provides an alternative modality for the restoration of SERCA2a activity in failing hearts.

In the decoy peptide or polypeptide of the present invention, the sequence "Ala-$X_2$-$X_3$-Ile-Glu" is necessary for its actions and functions. The $X_1$ and $X_4$ residues may have lots of variations. In this regard, the present invention encompasses any peptide or polypeptide comprising the sequence "Ala-$X_2$-$X_3$-Ile-Glu" so long as it retains functions or activities as a decoy to PP1.

The term used herein "peptide" means a linear molecule formed by linking amino acid residues via peptide bonds. The term used herein "polypeptide" means any polymer of (same or different) amino acids joined via peptide bonds.

The term used herein "decoy peptide or polypeptide" in conjunction with PLB is the designed peptide or polypeptide comprising a peptide sequence that mimics a connecting short loop of phosphorylated PLB and is capable of binding to PP1 in a competitive manner, thereby blocking the action of PP1.

The term used herein "PP1-mediated dephosphorylation" means the dephosphorylation of PLB by PP1.

The term used herein "competitive inhibition" with reference to decoy peptide (or polypeptide) means inhibition of dephosphorylation by binding competitively to PP1 to form the decoy peptide or polypeptide-PP1 complex. The decoy peptide or polypeptide binds to PP1 in such a way that it competes with phosphorylation sites of PLB for binding to PP1.

In certain embodiments, the decoy peptide or polypeptide of the present invention is cytosolic peptide or polypeptide. That is to say, in Formula I, $X_1$ and $X_4$ do not contain an amino acid domain which would preclude the decoy peptide or polypeptide from existing in the cytosol. For example, the amino acid domain includes membrane-spanning domains and organelle-targeting domains, but not limited to. In this regard, $X_1$ and $X_4$ encompass any amino acid residue(s) so long as they allow the decoy peptide or polypeptide to locate in the cytosol.

The decoy peptide or polypeptide may be in any length as long as it inhibits PP1-mediated dephosphorylation of PLB. For example, the decoy peptide or polypeptide may be in length of 5-100, 5-80, 5-60, 5-40, 5-30, 5-20, 5-15, 5-9, or 6-9 amino acids.

In certain embodiments of Formula I, $X_1$ represents 0-40, 0-30, 0-20, 0-10, 0-3, or 0-1 amino acid residue(s).

In Formula I, any amino acid(s) is located at $X_1$. In certain embodiments, $X_1$ consists of an amino acid sequence spanning 0-50, 0-40, 0-30, 0-20, 0-10, 0-3, or 0-1 amino acid residue(s) in the N-terminal direction of the amino acid position 15 of the amino acid sequence of PLB (see SEQ ID NO:10). In other embodiments, $X_1$ consists of 1 amino acid residue in the N-terminal direction of the amino acid position 15 of the amino acid sequence of PLB (see SEQ ID NO:10).

In certain embodiments of Formula I, $X_4$ represents 0-40, 0-30, 0-20, 0-10, or 0-3 amino acid residue(s).

In Formula I, any amino acid(s) is located at $X_4$. In certain embodiments, $X_4$ comprises an amino acid sequence spanning 0-50, 0-40, 0-30, 0-20, 0-10, or 0-3 amino acid residue(s) in the C-terminal direction of the amino acid position 19 of the amino acid sequence of PLB (see SEQ ID NO:10). In other embodiments, $X_4$ consists of an amino acid sequence spanning 0 or 3 amino acid residue(s) in the N-terminal direction of the amino acid position 19 of the amino acid sequence of PLB (see SEQ ID NO:10). In other embodiments, $X_4$ consists of an amino acid sequence spanning 3 amino acid residues in the N-terminal direction of the amino acid position 19 of the amino acid sequence of PLB (see SEQ ID NO:10).

In other embodiments, wherein $X_1$ is Arg.

In other embodiments, wherein $X_4$ is Met, Met-Pro, or Met-Pro-Gln.

The Ser residue at the amino acid position 16 ($Ser^{16}$) and Thr residue at the amino acid position 17 ($Thr^{17}$) of the amino acid sequence of PLB (see SEQ ID NO:10) are the phosphorylation sites located within the flexible loop region (the amino acid position 14-22 of the amino acid sequence of PLB (see SEQ ID NO:10)) of PLB. In Formula I, $X_2$ and $X_3$ represents the amino acid position occupied by the $Ser^{16}$ and $Thr^{17}$ in PLB, respectively.

In the present invention, the decoy peptide or polypeptide is designed by substituting the $Ser^{16}$ and/or $Thr^{17}$ residue(s) with a Glu or Asp residue. The decoy peptide or polypeptide comprising a Glu or Asp residue at $X_2$ and/or $X_3$ of Formula I is similar to phosphorylated PLB, thereby competing with the phosphorylation sites of PLB for binding to PP1.

In other embodiments, $X_2$ is Glu or Asp and $X_3$ is Thr, Glu, or Asp. In other embodiments, $X_2$ is Glu or Asp and $X_3$ is Thr.

In particular embodiments, the decoy peptide or polypeptide consists of the amino acid sequence selected from amino acid sequences as set forth in SEQ ID NOs:1-6. In particular embodiments, the decoy peptide or polypeptide consists of the amino acid sequence selected from amino acid sequences as set forth in SEQ ID NOs:1 and 3-6. In particular embodiments, the decoy peptide or polypeptide consists of the amino acid sequence selected from amino acid sequences as set forth in SEQ ID NOs:1, 3 and 6.

The sequences SEQ ID NOs:1-6 are as follows:

The sequence SEQ ID NO:1 is Arg-Ala-Glu-Thr-Ile-Glu-Met-Pro-Gln.

The sequence SEQ ID NO:2 is Arg-Ala-Ser-Glu-Ile-Glu-Met-Pro-Gln.

The sequence SEQ ID NO:3 is Arg-Ala-Asp-Thr-Ile-Glu-Met-Pro-Gln.

The sequence SEQ ID NO:4 is Ala-Glu-Thr-Ile-Glu-Met-Pro-Gln.

The sequence SEQ ID NO:5 is Arg-Ala-Glu-Thr-Ile-Glu-Met.

The sequence SEQ ID NO:6 is Arg-Ala-Glu-Thr-Ile-Glu.

The decoy peptide or polypeptide of the present invention may include peptide or polypeptide in which one or more of amino acids have side chain modification. Examples of side chain modifications include modifications of amino groups such as by reductive alkylation; amidination with methylacetimidate; acylation with acetic anhydride; carbamolyation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Any modification of cysteine residues must not affect the ability of the peptide to form the necessary disulphide bonds. It is also possible to replace the sulphydryl group of cysteine with selenium equivalents such that the peptide forms a diselenium bond in place of one or more of the disulphide bonds.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Proline residue may be modified by, for example, hydroxylation in the 4-position.

The decoy peptide or polypeptide of the present invention possesses much higher stability by modifications. For example, the decoy peptide or polypeptide has at least one amino acid residue protected with acetyl group, fluorenyl methoxy carbonyl group, formyl group, palmitoyl group, myristyl group, stearyl group or polyethylene glycol. In certain embodiments, the decoy peptide or polypeptide has at least one amino acid residue protected with acetyl group.

The term used herein "stability" refers to in vivo stability and storage stability (e.g., storage stability at room temperature) as well. The protection group described above protects the peptides from the attack of protease in vivo.

In other embodiments, the decoy peptide or polypeptide is further linked to a cell membrane-permeable peptide. In other embodiments, either the N-terminal and/or C-terminal of the decoy peptide or polypeptide is further linked to a cell membrane-permeable peptide.

For the decoy peptide or polypeptide of the present invention to be transferred into cardiaomyocytes, it may contain the cell membrane-permeable peptide. The term used herein "cell membrane-permeable peptide" means a peptide necessarily required to introduce a specific peptide (or protein) into a cell. Usually, it consists of 5-50 or more amino acid sequences.

The cell membrane-permeable peptide is a peptide capable of passing through the phospholipid bilayer of the cell membrane as it is. For example, it includes a Tat-derived peptide, a signal peptide (e.g., a cell-penetrating peptide), an arginine-rich peptide, a transportan, or an amphiphipatic peptide carrier, but not limited to (Morris, M. C. et al., *Nature Biotechnol.* 19: 1173-1176 (2001); Dupont, A. J. and Prochiantz, A., *CRC Handbook on Cell Penetrating Peptides*, Langel, Editor, CRC Press (2002); Chaloin, L. et al., *Biochemistry* 36(37): 11179-87 (1997); and Lundberg, P. and Langel, U., *J. Mol. Recognit.* 16(5): 227-233 (2003)). In addition to these naturally occurring peptides, various antennapedia-based peptides capable of crossing the cell membrane are known, including retroinverso and D-isomer peptides (Brugidou, J. et al., *Biochem Biophys Res Commun.* 214(2): 685-93 (1995); Derossi, D. et al., *Trends Cell Biol.* 8: 84-87 (1998)).

In certain embodiments, the TAT peptide (Tat-derived peptide) may be used as the cell membrane-permeable peptide.

The Tat protein, which originates from human immunodeficiency virus (HIV), consists of 86 amino acids and has cysteine-rich, basic and integrin-binding domains as major protein domains. Although the TAT peptide has a cell membrane-penetrating property only with the YGRKKRRQRRR (SEQ ID NO:11) (i.e., the 48$^{th}$ to 60$^{th}$ amino acids of Tat protein) sequence, it is known that a more efficient penetration is possible when it has a branched structure including several copies of the RKKRRQRRR sequence (Tung, C. H. et al., *Bioorg. Med. Chem.* 10: 3609-3614 (2002)). The various Tat peptides having cell membrane-penetrating ability are described in Schwarze, S. R. et al., *Science* 285: 1569-1572 (1999). In certain embodiments, the TAT peptide comprises the amino acid sequence as set forth in SEQ ID NO:11.

In addition, the decoy peptide or polypeptide of the present invention may further comprise the fusion protein for convenient purification, which includes but not limited to, with glutathione S-transferase (Pharmacia, USA), maltose binding protein (NEB, USA), FLAG (IBI, USA), or 6× His (hexahistidine; Quiagen, USA). In certain embodiments, the fusion protein may be purified by affinity chromatography. For example, elution buffer containing glutathione is employed for fusion proteins with glutathione S-transferase and Ni-NTA His-binding resin (Novagen, USA) is employed for fusion proteins with 6× His to purify the fusion protein of interest in a rapid and feasible manner.

In other embodiments, PLB is derived from human and its amino acid sequences are disclosed in NCBI (National Center for Biotechnology Information). Examples of Accession Numbers of the human PLB amino acid sequences in NCBI are AAA60109.1, AAA60083.1 and AAD55950.1.

According to the present invention, the term used herein "the decoy peptide or polypeptide" is intended to include functional equivalents of the decoy peptide or polypeptide. As used herein, the term "functional equivalent" refers to amino acid sequence variants (for example, variations at amino acid residues surrounding the necessary sequence Ala-X$_2$-X$_3$-Ile-Glu) having amino acid substitutions, additions or deletions in some of the amino acid sequence of the decoy peptide and polypeptide while simultaneously having similar or improved biologically activity when compared to the decoy peptide and polypeptide. The amino acid substitutions may be conservative substitutions. Examples of the conservative substitutions of naturally occurring amino acids include aliphatic amino acids (Gly, Ala, and Pro), hydrophobic amino acids (Ile, Leu, and Val), aromatic amino acids (Phe, Tyr, and Trp), acidic amino acids (Asp, and Glu), basic amino acids (His, Lys, Arg, Gln, and Asn), and sulfur-containing amino acids (Cys, and Met). The deletions of amino acids are located in a region which is not involved directly in the activity of the decoy peptides and polypeptides.

According to the present invention, the amino acid sequences of the decoy peptide and polypeptide available to the present invention are intended to include peptide sequences having substantial identity to the decoy peptide sequences. The term "substantial identity" as used herein means that the two amino acid sequences, when optimally aligned, such as by the program BLAST, GAP, or BESTFIT, or by visual inspection, share at least about 60%, 70%, 80%, 85%, 90%, or 95% sequence identity or sequence similarity. Methods of alignment of sequences for comparison are well-known in the art. Various programs and alignment algorithms are described in: Smith and Waterman, *Adv. Appl. Math.* 2:482 (1981), Needleman and Wunsch, *J. Mol. Bio.* 48:443 (1970), Pearson and Lipman, *Methods in Mol. Biol.* 24: 307-31 (1988), Higgins and Sharp, Gene 73:237-44 (1988), Higgins and Sharp, *CABIOS* 5:151-3 (1989), Corpet et al., *Nuc. Acids Res.* 16:10881-90 (1988), Huang et al., *Comp. Appl. BioSci.* 8:155-65 (1992) and Pearson et al., *Meth. Mol. Biol.* 24:307-31 (1994) presents a detailed consideration of sequence alignment methods and homology calculations.

The NCBI Basic Local Alignment Search Tool (BLAST) (Altschul et al., *J. Mol. Biol.* 215:403-10 (1990)) is available from several sources, including the NCBI and on the internet, for use in connection with the sequence analysis programs blastp, blasm, blastx, tblastn and tblastx. It can be accessed at www.ncbi.nlm.nih.gov/BLAST/. A description of how to determine sequence identity using this program is available at www.ncbi.nlm.nih.gov/BLAST/blast_help.html.

In another aspect of this invention, there is provided a pharmaceutical composition for preventing or treating a disease associated with PLB, comprising (a) a pharmaceutically effective amount of the decoy peptide or polypeptide of any one of the decoy peptides or polypeptides of the present invention; and (b) a pharmaceutically acceptable carrier.

The term used herein "preventing" with reference to a disease associated with PLB refers to the complete prevention of a disease associated with PLB, the prevention of occurrence of symptoms in a subject with the disease or the prevention of recurrence of symptoms in a subject with the disease.

The term used herein "treating" with reference to a disease associated with PLB refers to the partial or total elimination of symptoms or decrease in severity of symptoms of a disease associated with PLB in the subject.

The term used herein "pharmaceutically effective amount" with reference to a disease associated with PLB means a sufficient dose in the subject to which it is administered, to prevent or treat the symptoms, conditions, or diseases associated with PLB.

The term used herein "subject" is intended to encompass human, non-human mammal, or animal. Non-human mammals include livestock animals and companion animals, such as cattle, sheep, goats, equines, swine, dogs, and cats.

According to the present invention, the pharmaceutical composition comprising the decoy peptide or polypeptide as an active ingredient would be used to prevent or treat a disease associated with PLB.

The contractility of cardiomyocytes is directly regulated by intracellular $Ca^{2+}$ cycling, and SERCA2a plays a crucial role in $Ca^{2+}$ handling in cardiomyocytes. PLB is an endogenous inhibitor of SERCA2a and its inhibitory activity is enhanced via dephosphorylation by PP1.

Figure 1B:
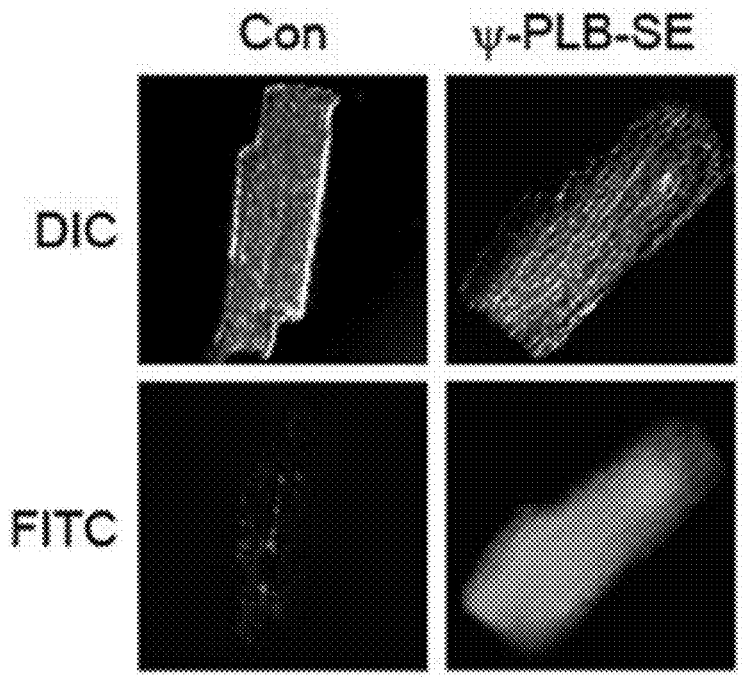
FIG. 1B represents intracellular uptake of decoy peptides in cardiomyocytes. The isolated cardiomyocytes were incubated with 1 μM of peptide solution for 1 hour at 37° C. Con, non-treated cell; ψpPLB-SE, decoy peptides labeled with FITC; DIC, differential interference contrast image; FITC, FITC fluorescent image.
Figure 1C:
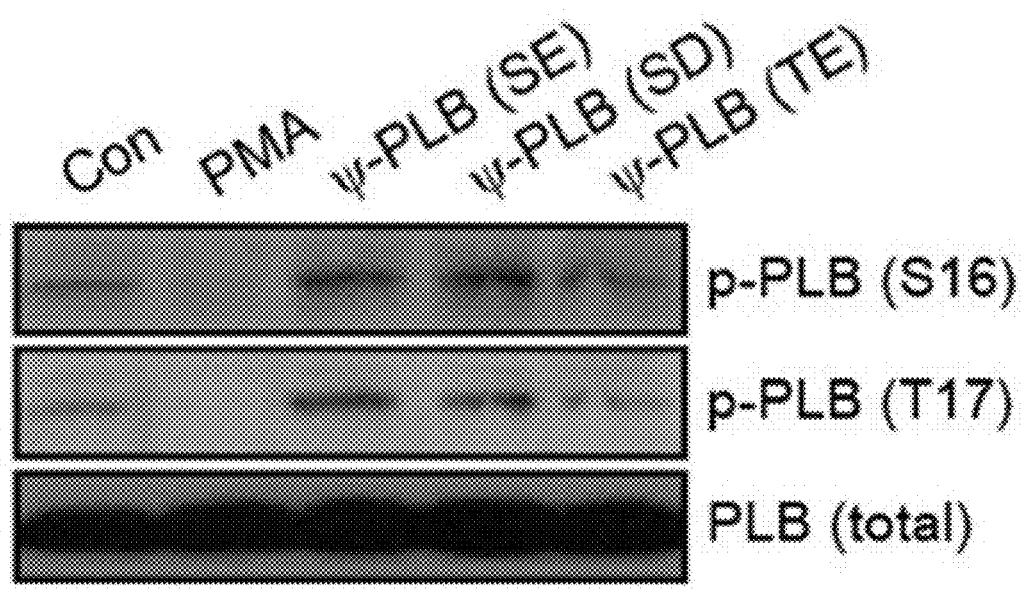
FIGS. 1C and 1D represent the increase in PLB phosphorylation by the decoy peptides (FIG. 1c) and shortened decoy peptides (FIG. 1d). Isolated adult cardiomyocytes were treated with 1 μM of indicated peptides for 45 min, and then with 1 μM of PMA for 15 min. Western blots of cell lysates were then probed with antibodies against phospho-PLB ($S^{16}$), phospho-PLB ($T^{17}$), total PLB, or GAPDH. The decoy peptides contain the following sequences: ψpPLB-SE, RAETIEMPQ (SEQ ID NO:1); ψpPLB-SD, RADTIEMPQ (SEQ ID NO:3); ψpPLB-TE, RASEIEMPQ (SEQ ID NO:2). The shortened decoy peptides contain the following sequences: ψpPLB-8-mer, AETIEMPQ (SEQ ID NO:4); ψpPLB-7-mer, RAETIEM (SEQ ID NO:5); ψpPLB-6-mer, RAETIE (SEQ ID NO:6); ψpPLB-5-mer: RAETI (SEQ ID NO:7). PMA, phorbol 12-myristate 13-acetate.
Figure 1D:
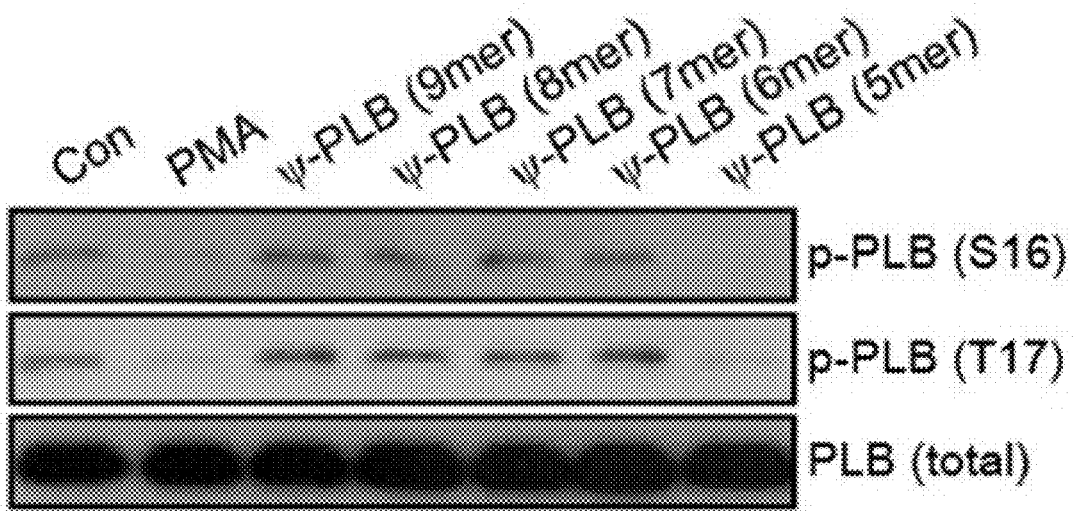

In the present invention, the decoy peptide significantly elevates phosphorylation levels of PLB (see FIGS. 1c and 1d). In addition, the decoy peptide increases contractile parameters in vitro (see FIGS. 2a-2d) and improves left ventricular developed pressure ex vivo (see FIGS. 3a and 3b). That is to say, the decoy peptide or polypeptide provides cardio-protective effects by restoring of SERCA2a activity and inotropic effect of enhancing myocardial contractility and thus the decoy peptide or polypeptide would be used to prevent or treat the diseases associated with PLB by inhibiting PP1-mediated dephosphorylation of PLB.

In certain embodiments, the disease associated with PLB is a heart disease. In certain embodiments, the heart disease is heart failure, ischemia, arrhythmia, myocardial infarction, congestive heart failure, transplant rejection, abnormal heart contractility, or abnormal $Ca^{2+}$ metabolism. In certain embodiments, the heart disease is heart failure or ischemia. In particular embodiments, the heart disease is heart failure.

The term used herein "heart failure" means a clinical symptom in which the stroke volume of the heart decreases below a normal value and the heart fails to supply enough blood to peripheral tissues. In other words, heart failure means the state in which the ability of the heart to pump blood is decreased due to various causes or enough blood cannot be supplied to the body even when the heart beats normally.

In other embodiments, the heart failure is induced by cardiac hypertrophy, coronary arteriosclerosis, myocardial infarction, valvular heart disease, hypertension, or cardiomyopathy.

In other embodiments, the pharmaceutical composition is an inotropic pharmaceutical composition.

According to the present invention, the pharmaceutical composition may contain pharmaceutically acceptable carriers. The pharmaceutically acceptable carrier may be conventional one for formulation, including lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but not limited to. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be orally or parentally administered. When the pharmaceutical composition of the present invention is administered parenterally, it can be done by intravenous, subcutaneous, intramuscular, abdominal or transdermal administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition, and physicians of ordinary skill in the art can determine an effective amount of the pharmaceutical composition for desired treatment. Generally, suitable dosage unit for human host is to administer with the pharmaceutical composition in 0.0001-100 mg/kg (body weight).

According to the conventional techniques known to those skilled in the art, the pharmaceutical composition may be formulated with pharmaceutically acceptable carrier and/or vehicle as described above, finally providing several forms including a unit dose form and a multi-dose form. Formulation may be oil or aqueous media, resuspension or emulsion, extract, powder, granule, tablet and capsule and further comprise dispersant or stabilizer.

In another aspect of this invention, there is provided a method for preparing a decoy peptide or polypeptide of PLB capable of inhibiting PP1-mediated dephosphorylation of PLB by a competitive inhibition, comprising (a) designing the decoy peptide or polypeptide of PLB by substituting a Ser residue at the amino acid position 16 and/or a Thr residue at the amino acid position 17 of the amino acid sequence of PLB (SEQ ID NO:10) with a Glu or Asp residue and selecting 0-95 surrounding amino acid residue(s) around the amino acid position 15-19 of the amino acid sequence of PLB (SEQ ID NO:10), such that the decoy peptide or polypeptide designed consists of a peptide sequence represented by the following Formula I: $X_1$-Ala-$X_2$-$X_3$-Ile-Glu-$X_4$ (I) wherein $X_1$ represents 0-50 amino acid residue(s), $X_2$ represents Ser, Glu, or Asp, $X_3$ represents Thr, Glu, or Asp and $X_4$ represents 0-50 amino acid residue(s), with the proviso that $X_2$ is not Ser when $X_3$ is Thr; and (b) preparing the decoy peptide or polypeptide designed in the step (a).

The present invention will be described in more detail as follows:

In the first step, the decoy peptide or polypeptide of PLB is designed by substituting a Ser residue at the amino acid position 16 and/or a Thr residue at the amino acid position 17 of the amino acid sequence of PLB (SEQ ID NO:10) with a Glu or Asp residue and selecting 0-95 surrounding amino acid residue(s) around the amino acid position 15-19 of the amino acid sequence of PLB (see SEQ ID NO:10), such that the decoy peptide or polypeptide designed consists of a peptide sequence represented by the following Formula I: $X_1$-Ala-$X_2$-$X_3$-Ile-Glu-$X_4$ (I) wherein $X_1$ represents 0-50 amino acid residue(s), $X_2$ represents Ser, Glu, or Asp, $X_3$ represents Thr, Glu, or Asp and $X_4$ represents 0-50 amino acid residue(s), with the proviso that $X_2$ is not Ser when $X_3$ is Thr.

In the decoy peptide or polypeptide of the present invention, the amino acid residues at the amino acid position 15, 18, and 19 of the amino acid sequence of PLB are Ala, Ile, and Glu (see SEQ ID NO:10).

According to the present invention, "Ala-$X_2$-$X_3$-Ile-Glu" of the decoy peptide or polypeptide sequence is necessary for its actions and functions. The surrounding amino acid residue(s) may have lots of variations. In this regard, the decoy peptide or polypeptide encompasses any surrounding amino acid residue(s) so long as it retains functions or activities as a decoy to PP1.

The surrounding amino acid residue(s) may be in any length as long as it inhibits PP1-mediated dephosphorylation of PLB. For example, the surrounding amino acid residue(s) may be in length of 0-95, 0-75, 0-55, 0-35, 0-15, 0-10, 0-4, or 1-4 amino acid.

In other embodiments, the surrounding amino acid residue(s) consists of (i) an amino acid sequence spanning 0-50, 0-40, 0-30, 0-20, 0-10, 0-3, or 0-1 amino acid residue(s) in the N-terminal direction of the amino acid position 15 and (ii) an amino acid sequence spanning 0-50, 0-40, 0-30, 0-20, 0-10, or 0-3 amino acid residue(s) in the C-terminal direction of the amino acid position 19 of the amino acid sequence of PLB (SEQ ID NO:10). In other embodiments, the amino acid residue in the N-terminal direction of amino acid position 15 is 1 amino acid residue and the amino acid residue(s) in the C-terminal direction of amino acid position 19 is 0 or 3 amino acid residue(s).

In other embodiment, the amino acid residue in the N-terminal direction of the amino acid position 15 is Arg. In other embodiments, the amino acid residue(s) in the C-terminal direction of the amino acid position 19 is is Met, Met-Pro, or Met-Pro-Gln.

In the present invention, the decoy peptide or polypeptide substituted the Ser$^{16}$ or Thr$^{17}$ residue(s) with a Glu or Asp residue increase the phosphorylation of PLB (see FIGS. 1c and 1d). Therefore, even if the only one of Ser$^{16}$ and Thr$^{17}$ residues is substituted with Glu or Asp residue, the decoy peptide or polypeptide could inhibit PP1-mediated dephosphorylation of PLB.

In certain embodiments, the decoy peptide or polypeptide is designed by substituting the Ser residue or both the Ser and the Thr residues with a Glu or Asp residue. In certain embodiments, the decoy peptide or polypeptide is designed by substituting only the Ser residue with a Glu or Asp residue.

In particular embodiments, the decoy peptide or polypeptide is designed such that it consists of the amino acid sequence selected from amino acid sequences as set forth in SEQ ID NOs:1-6. In particular embodiments, the decoy peptide or polypeptide is designed such that it consists of the amino acid sequence selected from amino acid sequences as set forth in SEQ ID NOs:1 and 3-6. In particular embodiments, the decoy peptide or polypeptide is designed such that it consists of the amino acid sequence selected from amino acid sequences as set forth in SEQ ID NOs:1, 3 and 6.

Following the step (a), the decoy peptide or polypeptide designed in the step (a) is prepared.

The decoy peptide or polypeptide of the present invention may be prepared according to recombinant DNA technologies or the solid-phase synthesis technique commonly employed in the art (Merrifield, R. B., *J. Am. Chem. Soc.*, 85: 2149-2154 (1963), Kaiser, E., Colescot, R. L., Bossinger, C. D., Cook, P. I., *Anal. Biochem.*, 34: 595-598 (1970)). The amino acids with α-amino and side-chain groups protected are attached to a resin. Then, after removing the α-amino protecting groups, the amino acids are successively coupled to obtain an intermediate.

In still another aspect of this invention, there is provided a method for preventing or treating a disease associated with PLB, comprising administering to a subject in need thereof (a) a pharmaceutically effective amount of the decoy peptide or polypeptide of any one of the decoy peptides or polypeptides of the present invention; and (b) a pharmaceutically acceptable carrier.

In certain embodiments, the disease associated with PLB is a heart disease. In certain embodiments, the heart disease is heart failure, ischemia, arrhythmia, myocardial infarction, congestive heart failure, transplant rejection, abnormal heart contractility, or abnormal Ca$^{2+}$ metabolism. In certain embodiments, the heart disease is heart failure or ischemia. In particular embodiments, the heart disease is heart failure.

In other embodiments, the heart failure is induced by cardiac hypertrophy, coronary arteriosclerosis, myocardial infarction, valvular heart disease, hypertension, or cardiomyopathy.

The features and advantages of this invention will be summarized as follows:

(a) The present invention provides a decoy peptide or polypeptide capable of inhibiting PP1-mediated dephosphorylation of PLB by a competitive inhibition and a pharmaceutical composition for preventing or treating a disease associated with PLB comprising the decoy peptide or polypeptide of the present invention as an active ingredient.

(b) The present invention provides a method for preparing the decoy peptide or polypeptide of PLB and preventing or treating a disease associated with PLB.

(c) It is noteworthy that the decoy peptide or polypeptide of the present invention significantly elevates phosphorylation levels of PLB by inhibiting PP1-mediated dephosphorylation. In addition, the decoy peptide or polypeptide provides cardio-protective effects by restoring of SERCA2a activity and inotropic effect of enhancing myocardial contractility.

(d) The present invention will contribute greatly to the prevention or treatment of diseases associated with PLB.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods
Decoy Peptides

The decoy peptides were derived from the PLB protein sequence (SEQ ID NO:10) surrounding the phosphorylation sites Ser$^{16}$ and Thr$^{17}$:RAS$^{16}$T$^{17}$IEMPQ. The peptides were conjugated via a cystein-cystein bond at their N termini to the cell penetrating peptide TAT (YGRKKRRQRRR (SEQ ID NO:11)) to facilitate uptake into cells. The peptides used in this invention were as follows: ψpPLB-wt, RASTIEMPQ (SEQ ID NO:8); ψpPLB-SE, RAETIEMPQ (SEQ ID NO:1); ψpPLB-TE, RASEIEMPQ (SEQ ID NO:2); ψPLB-SD, RADTIEMPQ (SEQ ID NO:3). In addition, shortened ψPLB-SE peptides were also tested: 8-mer, AETIEMPQ (SEQ ID NO:4); 7-mer, RAETIEM (SEQ ID NO:5); 6-mer, RAETIE (SEQ ID NO:6); 5-mer, RAETI (SEQ ID NO:7). All of the peptides were synthesized and modified by AnyGen (Gwangju, Korea) and dissolved in distilled water to a stock concentration of 1 mM. Peptides were >95% pure. The decoy peptides were treated for 1 h at a final concentration of 1 μM. Cell viability and morphology were not significantly affected by the peptides Isolation of Adult Rat Ventricular Myocytes Ventricular myocytes were isolated from SD rat hearts as previously described [33] with minor modifications. Male rats of 8-12 weeks of age (250-320 g) were used. In brief, rats were anesthetized by the inhalation of isofluran (0.5%) for 5 min. The heart was quickly removed from the chest and the aorta was retrogradely perfused at 37° C. for 3 min with calcium-free Tyrode buffer (137 mM NaCl, 5.4 mM KCl, 1 mM MgCl$_2$, 10 mM glucose, 10 mM HEPES [pH 7.4], 10 mM 2, 3-butanedione monoxime, and 5 mM taurine) gassed with 100% $O_2$. The enzymatic digestion was then initiated by adding collagenase type B (0.35 U/ml; Roche) and hyaluronidase (0.1 mg/ml; Worthington) to the perfusion solution. When the heart became swollen after 10 min of digestion, the left ventricle was quickly removed, cut into several chunks, and further digested in a shaker (60-70 rpm) for 10 min at 37° C. in the same enzyme solution. The supernatant containing the dispersed myocytes was then filtered through a cell strainer (100 μm in pore size, BD Falcon) and gently centrifuged at 500 rpm for 1 min. Extracellular $Ca^{2+}$ was incrementally added back to a concentration of 1.25 mM over a span of 30 min to avoid the $Ca^{2+}$ paradox. This procedure usually yielded ≥80% viable rod-shaped ventricular myocytes with clear sarcomere striations. Myocytes with obvious sarcolemmal blebs or spontaneous contractions were discarded.

Fluorescence Microscopy

To confirm cellular uptake of the peptides, ψPLB-SE was labeled with FITC. The isolated cardiomyocytes were plated onto a laminin-coated glass plate and cultured in modified Eagle's Medium (MEM) with Hanks' Balanced Salt solution, supplemented with 2 mM L-carnitine, 5 mM creatine and 5 mM taurine, and 100 IU/ml penicillin. The cells were exposed to 1 μM FITC-labeled ψpPLB-SE for 1 h, and then washed twice with Tyrode solution. Fluorescence images were visualized using a Leica DMRBE microscope (LabCommerce Inc.) equipped with a 63× (1.4 NA) oil objective and fluorescein FITC-optimized filter sets (OmegaR Optical Inc.). Images were acquired using a CoolSNAP TMfx CCD camera (Photometrics) and analyzed with Metamorph imaging software (Universal Imaging Co.).

Western Blot Analysis.

Heart lysates (50 μg) in SDS sample buffer were run on a SDS-PAGE gel and then transferred to a PVDF membrane (Bio-Rad). The membrane was blocked with a 5% skim milk solution and then incubated overnight with antibodies directed against PLB (Affinity Bioreagents), phospho-PLB ($Ser^{16}$, Cell Signaling), phospho-PLB ($Thr^{17}$, Badrilla), SERCA2a (Santa Cruz), Caspase 3 (Cell Signaling), or GAPDH (Santa Cruz). The membranes were then incubated with a secondary antibody conjugated to horseradish peroxidase (Jackson Immuno Research) and developed using the Western Lighting chemiluminescence reagent (Perkin Elmer).

Cell Contractility and Intracellular $Ca^{2+}$ Transient Measurements

The mechanical properties of ventricular myocytes were assessed using a video-based edge detection system (IonOptix), as previously described [34]. In brief, laminin-coated coverslips with attached cells were placed in a chamber mounted on the stage of an inverted microscope (Nikon Eclipse TE-100F) and perfused (about 1 ml/min at 37° C.) with Tyrode buffer (137 mM NaCl, 5.4 mM KCl, 1 mM $CaCl_2$, 1 mM $MgCl_2$, 10 mM glucose, and 10 mM HEPES [pH 7.4]). The cells were field-stimulated at a frequency of 3 Hz (30 V) using a STIM-AT stimulator/thermostat placed on a HLD-CS culture chamber/stim holder (Cell Micro Controls). The myocyte of interest was displayed on a computer monitor using an IonOptix Myo-Cam camera, which rapidly scanned the image area every 8.3 ms, so that the amplitude and velocity of shortening or relengthening were recorded with fidelity. Changes in cell length during shortening and relengthening were captured and analyzed using soft edge software (IonOptix). The cardiomyocytes were loaded with 0.5 μM Fura2-AM (Molecular Probes), a $Ca^{2+}$-sensitive indicator, for 15 min at 37° C. Fluorescence emissions were recorded simultaneously with the contractility measurements using Myocyte calcium and contractility recording system (IonOptix). Cardiomyocytes were exposed to light emitted by a 75 W halogen lamp through either a 340 or 380 nm filter while being field-stimulated as described above. Fluorescence emissions were detected between 480 and 520 nm by a photomultiplier tube after initial illumination at 340 nm for 0.5 ms and then at 380 nm for the duration of the recording protocol. The 340 nm excitation scan was then repeated at the end of the protocol, and qualitative changes in the intracellular $Ca^{2+}$ concentration were inferred from the ratio of the Fura fluorescence intensity at both wavelengths.

Isolated Perfused Heart Experiments

Rats were anesthetized by inhalation of isofluran (0.5%) for 5 min. The heart was quickly removed and placed in cold oxygenated Tyrode solution (137 mM NaCl, 5.4 mM KCl, 1 mM $MgCl_2$, 10 mM glucose, 1 mM $CaCl_2$, 10 mM HEPES [pH 7.4], 100% $O_2$). The aorta was cannulated and perfused by the Langendorff method with oxygenated Tyrode solution at constant pressure (65 mmHg, temperature 37±0.2° C.). A latex water-filled balloon was inserted into the left ventricular chamber and connected to a pressure transducer (AD Instruments) for continuous measurement of heart performance. Heart rate, left ventricular developed pressure (LVDP), and the first derivatives of LV pressure (LV+dP/dt max and LV−dP/dt max) were all recorded using PowerLab Chart Systems (AD Instruments). The balloon volume was adjusted in 250-300 μl to result in a measured end diastolic pressure in the range of 6-10 mmHg. After a 30 min stabilization period, the hearts were subjected to 20 min of no-flow to induce global ischemia, followed by 30 min of reperfusion. Perfusion of decoy peptides was performed at a final concentration of 1 μM.

Statistics

Where appropriate, the data are expressed as means±SDs. Comparisons of group means were made by using either a Student's t-test or a one-way ANOVA with Bonferroni correction (Statview version 5.0, SAS). A P-value of <0.05 was considered to be statistically significant.

Results

Decoy Peptide

PLB is composed of a cytoplasmic helix at the N-terminus, a transmembrane helix at the C-terminus, and a flexible loop that connects the two helices (FIG. 1a, left). The phosphorylation sites $Ser^{16}$ and $Thr^{17}$ reside in the connecting loop region. We synthesized a 9-mer peptide (RASTI-EMPQ (SEQ ID NO:8)) that exactly matched the nine amino acid sequence of the loop region and coupled it to a cell-permeable peptide TAT through a disulfide bond to yield ψpPLB-wt. In addition, we generated similar TAT-coupled peptides, in which the Ser or Thr residue corresponding to $Ser^{16}$ or $Thr^{17}$ of PLB were individually replaced by Glu to yield ψpPLB-SE or ψpPLB-TE, respectively (FIG. 1a, right). These peptides were labeled with FITC and added to the cultured cardiomyocytes isolated from rat left ventricles. Observation under a fluorescent microscope revealed an efficient intracellular uptake of the peptides in virtually all of the cardiomyocytes (FIG. 1b). This experiment ensured that the cardiomyocytes efficiently took up the peptides, and so un-labeled peptides were then used for the rest of the experiments.

It is known that the treatment of cardiomyocytes with PMA (phorbol 12-myristate 13-acetate) significantly reduces phosphorylation of PLB through activation of PKCα. Pre-treatment with ψpPLB-SE, but not with ψpPLB-wt, significantly blocked the PMA-induced dephosphorylation of PLB at both $Ser^{16}$ and $Thr^{17}$. ψpPLB-TE also blocked dephosphorylation but was less effective than ψpPLB-SE (FIG. 1c). The elevated phosphorylation levels of PLB seen after ψPLB-SE treatment were slightly but significantly higher than the basal levels. Considering that PP1 is the only protein phosphatase known to dephosphorylate PLB, these data demonstrated that ψPLB-SE served as an effective decoy peptide to competitively inhibit PP1-mediated dephosphorylation of PLB.

ψpPLB-SD, in which Ser$^{16}$ was replaced with Asp, was as effective as ψPLB-SE in elevating the phosphorylation levels of PLB (FIG. 1c). We synthesized shortened ψpPLB-SE peptides consisting of AETIEMPQ (SEQ ID NO:4) (ψpPLB-8-mer), RAETIEM (SEQ ID NO:5) (ψpPLB-7-mer), RAETIE (SEQ ID NO:6) (ψpPLB-6-mer), and RAETI (SEQ ID NO:7) (ψpPLB-5-mer). Among these peptides, only ψpPLB-5-mer was ineffective in elevating the phosphorylation levels of PLB (FIG. 1d). Therefore, it appeared that ASTIE (SEQ ID NO:9) is the minimal amino acid sequence required, and that the Ser residue can be replaced by either Glu or Asp to create an effective decoy peptide for PP1.

ψPLB-SE Increases Cardiomyocyte Contractility

Figure 2A:
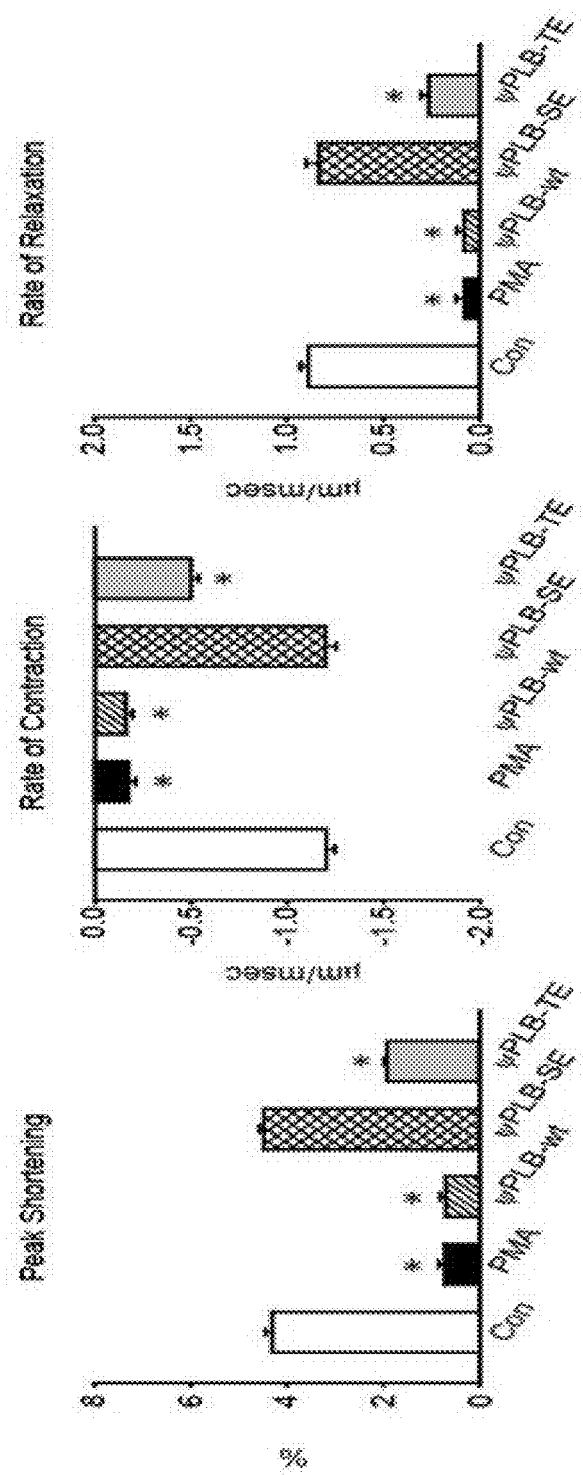
FIGS. 2A, 2B, 2C and 2D represent the increase in cardiac contractility by the decoy peptides. Isolated adult cardiomyocytes were treated with 1 μM of indicated peptides for 45 min, and then with 1 μM of PMA for 15 min. Contractile parameters were then determined.
Figure 2B:
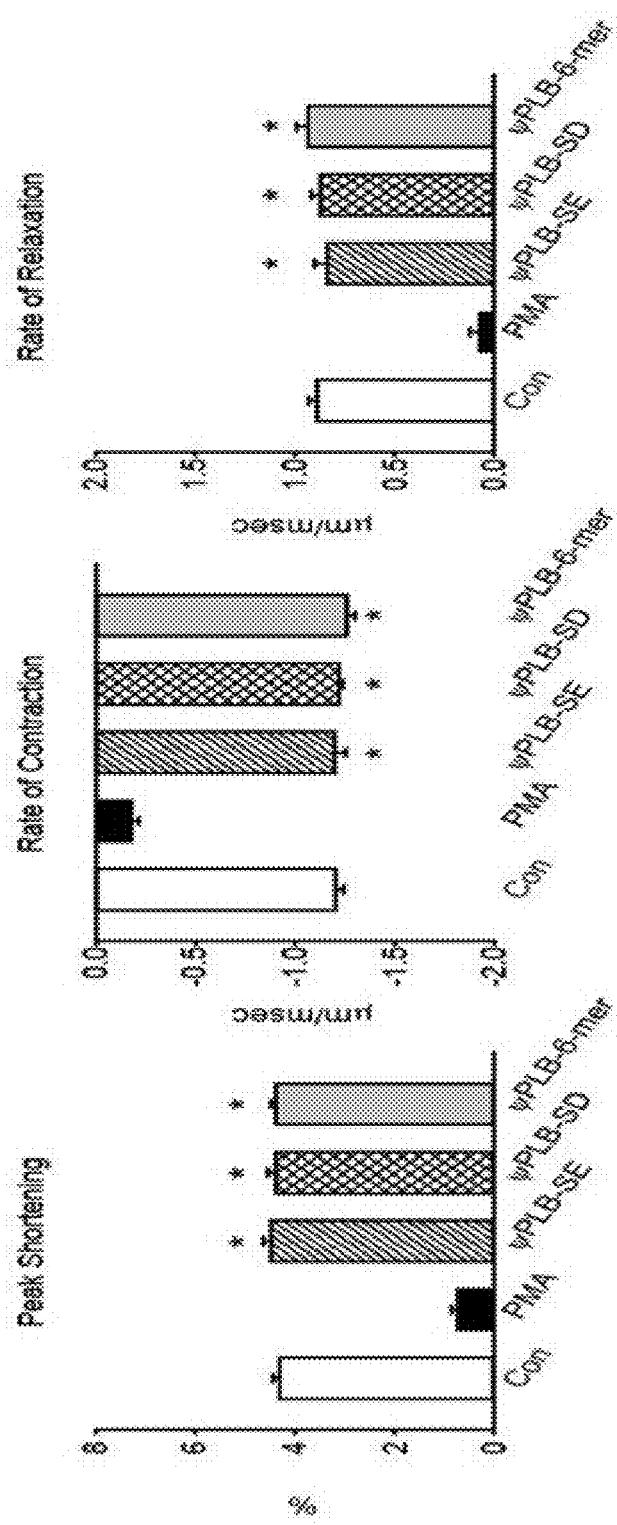
Figure 2C:
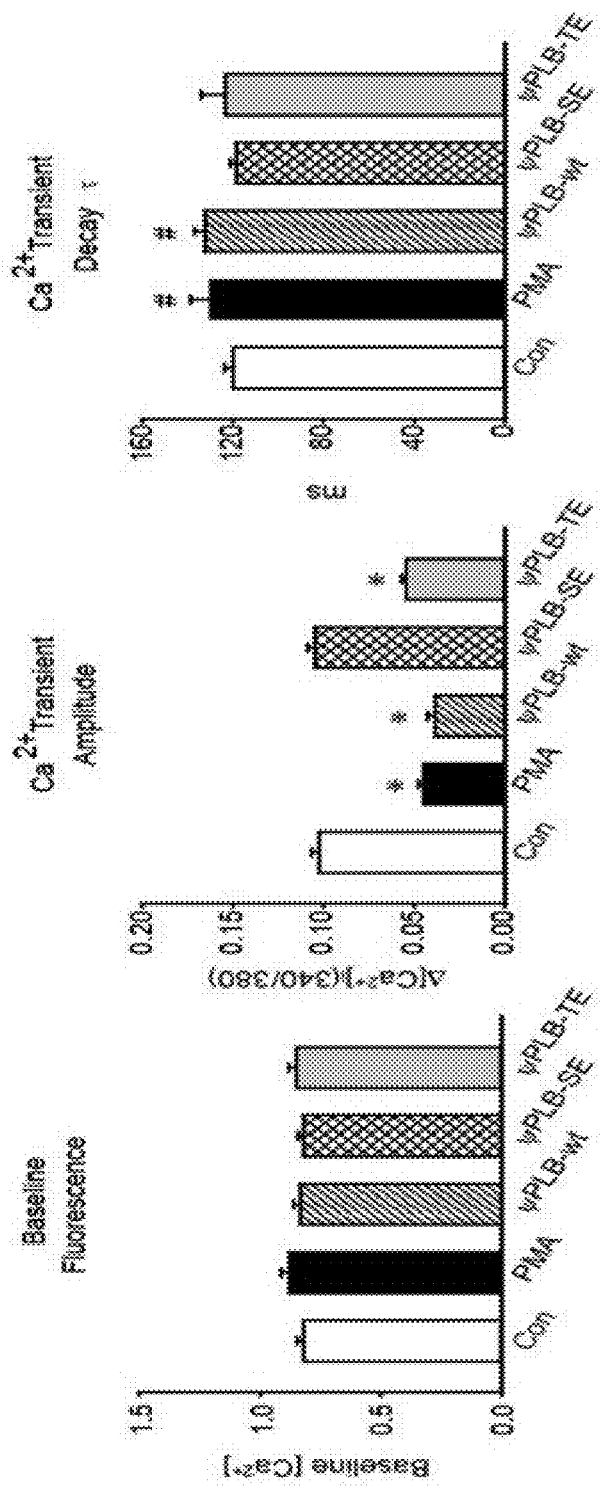
Figure 2D:
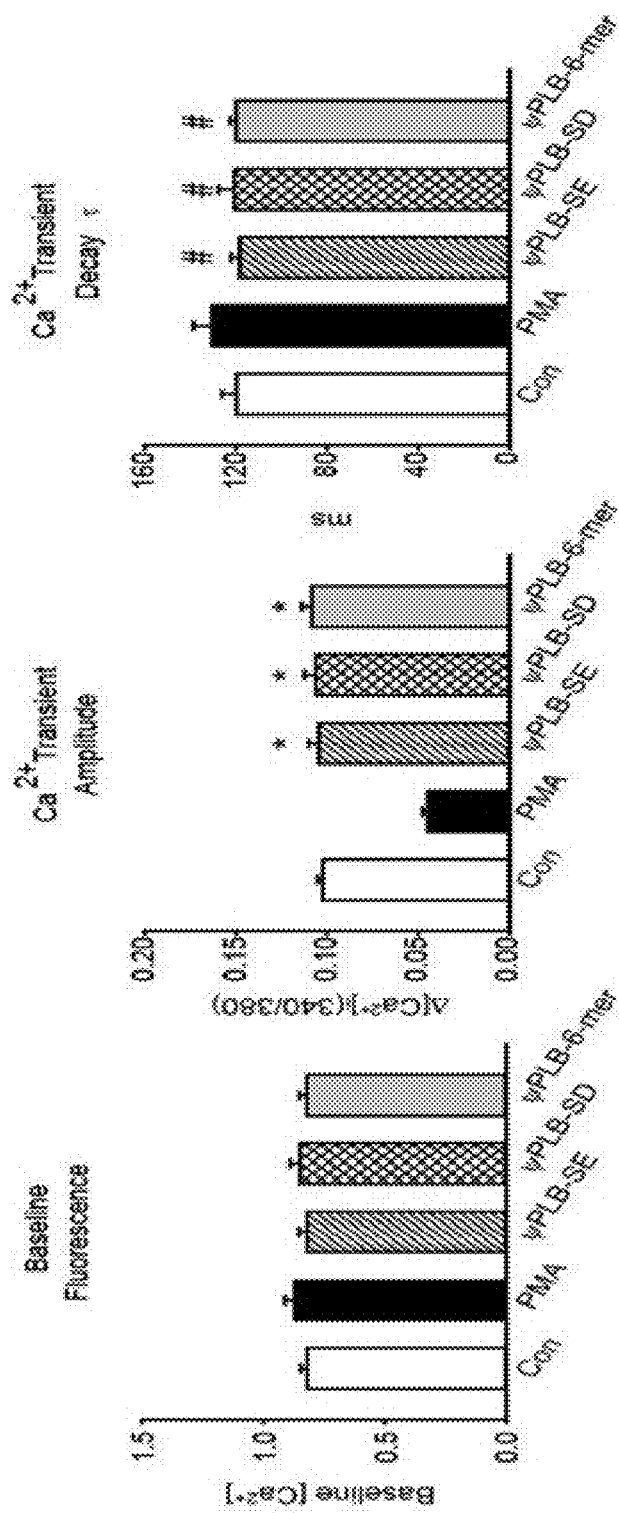

We next tested whether ψPLB-SE affected cardiomyocyte contractility. Isolated adult cardiomyocytes were pre-treated with the peptides and then treated with PMA. As indicated by the reduced contractile parameters including peak shortening, and the rates of contraction and relaxation, contractility was significantly reduced by PMA. While ψPLB-wt and ψpPLB-TE elicited no or only marginal effects on contractility, ψPLB-SE completely prevented the PMA-induced reduction in contractility (FIG. 2a). PMA also evoked a significant reduction in the Ca$^{2+}$ transient amplitude and a significant increase in the time constant of the Ca$^{2+}$ transient decay (τ). These PMA-induced defects were completely reversed by pre-treatment of ψpPLB-SE, while the effects of ψpPLB-wt and ψpPLB-TE on intracellular Ca$^{2+}$ handling were negligible or marginal (FIG. 2b). These data indicated that the restored phosphorylation levels of endogenous PLB by pre-treatment of ψpPLB-SE yielded a normalized contractility. Both ψpPLB-SD and ψpPLB-6-mer were as effective as ψpPLB-SE in the preservation of contractility and Ca$^{2+}$ handling (FIGS. 2c and 2d).

ψPLB-SE Improves Functional Recovery After Ischemia/Reperfusion Ex Vivo

Figure 3A:
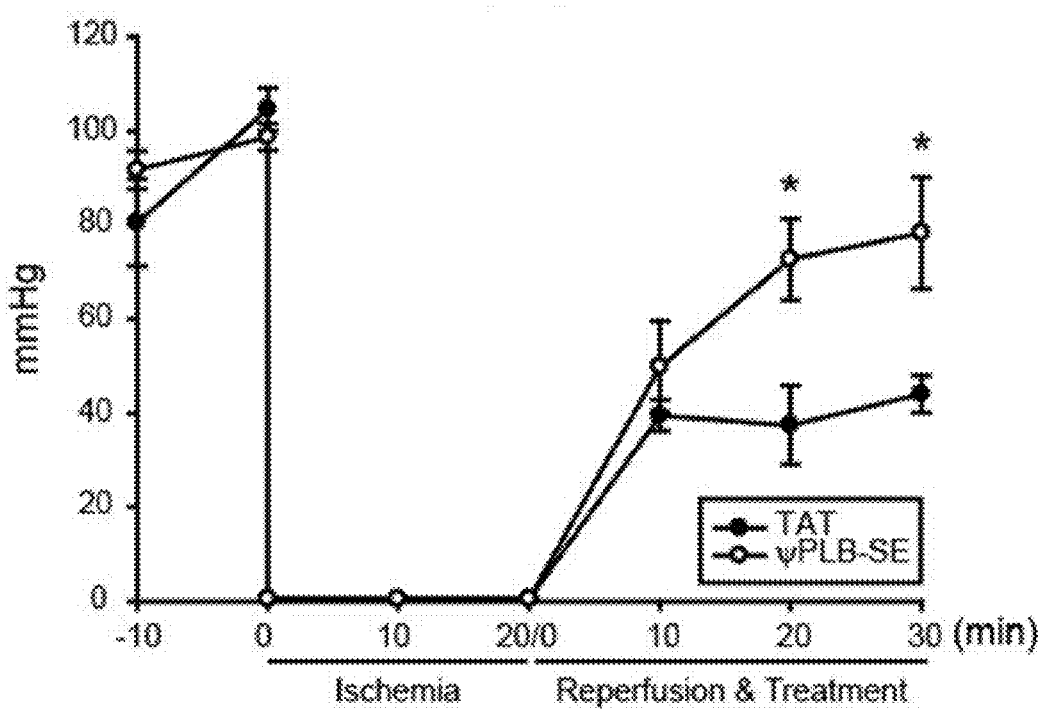
FIGS. 3A and 3B represent the postischemic cardiac performance ex vivo.
Figure 3B:
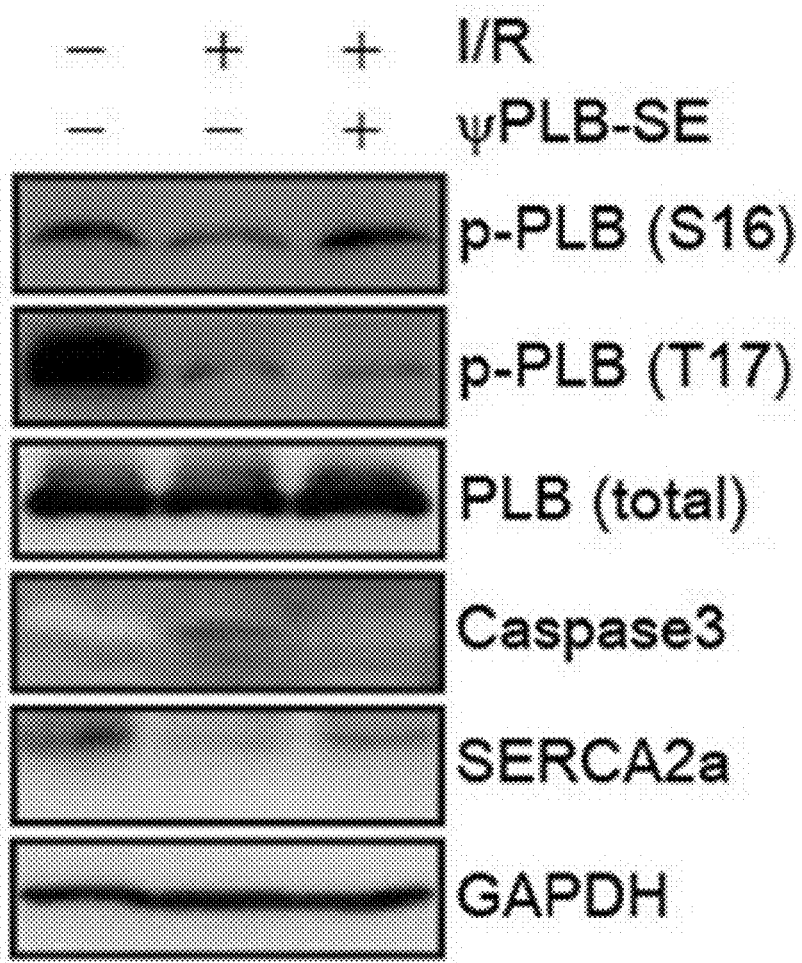

We further examined the benefits of ψpPLB-SE during ischemia/reperfusion (I/R) ex vivo. Rat hearts were Langendorff-perfused, subjected to 20 min of no-flow to induce global ischemia, and then 30 min of reperfusion. The developed pressure of left ventricles was significantly lowered (37-44 mmHg vs. 80-100 mmHg at pre-ischemia) by I/R. At the time of reperfusion, ψpPLB-SE or a control peptide TAT was added to the reperfusion solutions. While TAT had no effects, ψpPLB-SE significantly elevated the developed pressure (73-78 mmHg) (FIG. 3a). At the end of the experiment, lysates of the hearts were prepared and subjected to Western blotting. Phosphorylation of PLB at both Ser$^{16}$ and Thr$^{17}$ was significantly reduced by I/R, and phosphorylation at Ser$^{16}$ was significantly recovered by ψpPLB-SE. In addition, cell death-related Caspase 3 was activated by I/R, which was completely reversed by ψpPLB-SE (FIG. 3b). Collectively, these data showed that ψpPLB-SE improved functional recovery after I/R, at least in part, through elevating the phosphorylation levels of PLB at Ser$^{16}$.

Discussion

SERCA2a is a crucial regulator of intracellular Ca$^{2+}$ handling in cardiomyocytes, and its role in heart failure and I/R injury is well established [6]. Therefore, modalities that normalize SERCA2a levels and/or activity could have significant therapeutic potentials. One such approach involves a gene delivery-mediated recovery of suppressed SERCA2a levels in failing hearts. This approach is effective in animal models of heart failure [13-16], and recently has been proven to be safe and effective in end-stage human heart failure patients [17, 18].

PLB is an endogenous inhibitor of SERCA2a and is therefore a potential target for modulation of SERCA2a activity. Down-regulation of PLB with antisense RNA [35] or small interfering RNA [36] partially restored SERCA2a activity and cardiomyocyte contractility. A dominant negative form of PLB, K3E/R14E, designed to disrupt the structural integrity of endogenous PLB, enhanced SERCA2a activity in neonatal and adult cardiomyocytes [35].

In this study, we showed that ψpPLB-SE prevented dephosphorylation of PLB by serving as a decoy peptide for PP1. Interestingly, we found that ψpPLB-TE was not as effective as ψPLB-SE (FIG. 1c). Although a structural insight is currently unavailable, it is possible that PLB with a phosphorylation at Ser$^{16}$ is a better substrate for PP1 than PLB with a phosphorylation at Thr$^{17}$. It is notable that phosphorylation at Thr$^{17}$ occurs only subsequent to phosphorylation at Ser$^{16}$ during β-adrenergic stimulation [36]. Therefore, PLB with phosphorylation only at Thr$^{17}$ may not exist in vivo. In conclusion, we showed that ψpPLB-SE elicited cardio-protective effects by restoring SERCA2a activity. As a short peptide, ψpPLB-SE has several therapeutic advantages over the siRNAs or mutant PLB proteins. Further experiments are warranted to determine if ψPLB-SE is effective in various surgical and genetic models of heart failure.

Having described a preferred embodiment of the present invention, it is to be understood that variants and modifications thereof falling within the spirit of the invention may become apparent to those skilled in this art, and the scope of this invention is to be determined by appended claims and their equivalents.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

REFERENCES

1. Lopez A D, Mathers C D, Ezzati M, Jamison D T, Murray C J. Global and regional burden of disease and risk factors, 2001: systematic analysis of population health data. *Lancet.* 2006 May 27; 367(9524): 1747-57.
2. Mathers C D, Loncar D. Projections of global mortality and burden of disease from 2002 to 2030. *PLoS Med.* 2006 November; 3(11): e442.
3. Mathers C D, Boerma T, Ma Fat D. Global and regional causes of death. *Br Med Bull.* 2009; 92: 7-32.
4. Houser S R, Piacentino V, 3rd, Weisser J. Abnormalities of calcium cycling in the hypertrophied and failing heart. *J Mol Cell Cardiol.* 2000 September; 32(9): 1595-607.
5. Houser S R, Margulies K B. Is depressed myocyte contractility centrally involved in heart failure? *Circ Res.* 2003 Mar. 7; 92(4): 350-8.
6. Lehnart S E, Maier L S, Hasenfuss G. Abnormalities of calcium metabolism and myocardial contractility depression in the failing heart. *Heart Fail Rev.* 2009 December; 14(4): 213-24.
7. Bers D M, Guo T. Calcium signaling in cardiac ventricular myocytes. *Ann NY Acad Sci.* 2005 June; 1047: 86-98.

8. Schaub M C, Hefti M A, Zaugg M. Integration of calcium with the signaling network in cardiac myocytes. *J Mol Cell Cardiol.* 2006 August; 41(2): 183-214.
9. MacLennan D H, Kranias E G. Phospholamban: a crucial regulator of cardiac contractility. *Nat Rev Mol Cell Biol.* 2003 July; 4(7): 566-77.
10. Arai M, Matsui H, Periasamy M. Sarcoplasmic reticulum gene expression in cardiac hypertrophy and heart failure. *Circ Res.* 1994 April; 74(4): 555-64.
11. Hasenfuss G, Reinecke H, Studer R, Meyer M, Pieske B, Holtz J, et al. Relation between myocardial function and expression of sarcoplasmic reticulum Ca(2+)-ATPase in failing and nonfailing human myocardium. *Circ Res.* 1994 September; 75(3): 434-42.
12. Meyer M, Schillinger W, Pieske B, Holubarsch C, Heilmann C, Posival H, et al. Alterations of sarcoplasmic reticulum proteins in failing human dilated cardiomyopathy. *Circulation.* 1995 Aug. 15; 92(4): 778-84.
13. Miyamoto M I, del Monte F, Schmidt U, DiSalvo T S, Kang Z B, Matsui T, et al. Adenoviral gene transfer of SERCA2a improves left-ventricular function in aortic-banded rats in transition to heart failure. *Proc Natl Acad USA.* 2000 Jan. 18; 97(2): 793-8.
14. del Monte F, Hajjar R J, Harding S E. Overwhelming evidence of the beneficial effects of SERCA gene transfer in heart failure. *Circ Res.* 2001 Jun. 8; 88(11): E66-7.
15. Sakata S, Lebeche D, Sakata Y, Sakata N, Chemaly E R, Liang L, et al. Transcoronary gene transfer of SERCA2a increases coronary blood flow and decreases cardiomyocyte size in a type 2 diabetic rat model. *Am J Physiol Heart Circ Physiol.* 2007 February; 292(2): H1204-7.
16. Kawase Y, Ly H Q, Prunier F, Lebeche D, Shi Y, Jin H, et al. Reversal of cardiac dysfunction after long-term expression of SERCA2a by gene transfer in a pre-clinical model of heart failure. *J Am Coll Cardiol.* 2008 Mar. 18; 51(11): 1112-9.
17. Jaski B E, Jessup M L, Mancini D M, Cappola T P, Pauly D F, Greenberg B, et al. Calcium upregulation by percutaneous administration of gene therapy in cardiac disease (CUPID Trial), a first-in-human phase ½ clinical trial. *J Card Fail* 2009 April; 15(3): 171-81.
18. Jessup M, Greenberg B, Mancini D, Cappola T, Pauly D F, Jaski B, et al. Calcium Upregulation by Percutaneous Administration of Gene Therapy in Cardiac Disease (CUPID): a phase 2 trial of intracoronary gene therapy of sarcoplasmic reticulum Ca2+-ATPase in patients with advanced heart failure. *Circulation.* 2011 Jul. 19; 124(3): 304-13.
19. Le Peuch C J, Haiech J, Demaille J G. Concerted regulation of cardiac sarcoplasmic reticulum calcium transport by cyclic adenosine monophosphate dependent and calcium-calmodulin-dependent phosphorylations. *Biochemistry.* 1979 Nov. 13; 18(23): 5150-7.
20. James P, Inui M, Tada M, Chiesi M, Carafoli E. Nature and site of phospholamban regulation of the Ca2+ pump of sarcoplasmic reticulum. *Nature.* 1989 Nov. 2; 342 (6245): 90-2.
21. Mattiazzi A, Mundina-Weilenmann C, Guoxiang C, Vittone L, Kranias E. Role of phospholamban phosphorylation on Thr17 in cardiac physiological and pathological conditions. *Cardiovasc Res.* 2005 Dec. 1; 68(3): 366-75.
22. MacDougall L K, Jones L R, Cohen P. Identification of the major protein phosphatases in mammalian cardiac muscle which dephosphorylate phospholamban. *Eur J Biochem.* 1991 Mar. 28; 196(3): 725-34.
23. Steenaart N A, Ganim J R, Di Salvo J, Kranias E G. The phospholamban phosphatase associated with cardiac sarcoplasmic reticulum is a type 1 enzyme. *Arch Biochem Biophys.* 1992 Feb. 14; 293(1): 17-24.
24. Schwinger R H, Munch G, Bolck B, Karczewski P, Krause E G, Erdmann E. Reduced Ca(2+)-sensitivity of SERCA 2a in failing human myocardium due to reduced serin-16 phospholamban phosphorylation. *J Mol Cell Cardiol.* 1999 March; 31(3): 479-91.
25. Mishra S, Gupta R C, Tiwari N, Sharov V G, Sabbah H N. Molecular mechanisms of reduced sarcoplasmic reticulum Ca(2+) uptake in human failing left ventricular myocardium. *J Heart Lung Transplant.* 2002 March; 21(3): 366-73.
26. Sande J B, Sjaastad I, Hoen I B, Bokenes J, Tonnessen T, Holt E, et al. Reduced level of serine(16) phosphorylated phospholamban in the failing rat myocardium: a major contributor to reduced SERCA2 activity. *Cardiovasc Res.* 2002 Feb. 1; 53(2): 382-91.
27. Neumann J, Eschenhagen T, Jones L R, Linck B, Schmitz W, Scholz H, et al. Increased expression of cardiac phosphatases in patients with end-stage heart failure. *J Mol Cell Cardiol.* 1997 January; 29(1): 265-72.
28. Huang B, Wang S, Qin D, Boutjdir M, El-Sherif N. Diminished basal phosphorylation level of phospholamban in the postinfarction remodeled rat ventricle: role of beta-adrenergic pathway, G(i) protein, phosphodiesterase, and phosphatases. *Circ Res.* 1999 Oct. 29; 85(9): 848-55.
29. Ta H M, Nguyen G T, Jin H M, Choi J, Park H, Kim N, et al. Structure-based development of a receptor activator of nuclear factor-kappaB ligand (RANKL) inhibitor peptide and molecular basis for osteopetrosis. *Proc Natl Acad USA.* 2010 Nov. 23; 107(47): 20281-6.
30. Law J H, Li Y, To K, Wang M, Astanehe A, Lambie K, et al. Molecular decoy to the Y-box binding protein-1 suppresses the growth of breast and prostate cancer cells whilst sparing normal cell viability. *PLoS One.* 2010; 5(9).
31. Yamaguchi H, Durell S R, Feng H, Bai Y, Anderson C W, Appella E. Development of a substrate-based cyclic phosphopeptide inhibitor of protein phosphatase 2Cdelta, Wip1. *Biochemistry.* 2006 Nov. 7; 45(44): 13193-202.
32. Hayashi R, Tanoue K, Durell S R, Chatterjee D K, Jenkins L M, Appella D H, et al. Optimization of a cyclic peptide inhibitor of Ser/Thr phosphatase PPM1D (Wip1). *Biochemistry.* 2011 May 31; 50(21): 4537-49.
33. Ren J, Wold L E. Measurement of Cardiac Mechanical Function in Isolated Ventricular Myocytes from Rats and Mice by Computerized Video-Based Imaging. *Biol Proced Online.* 2001 Dec. 11; 3: 43-53.
34. Zhou Y Y, Wang S Q, Zhu W Z, Chruscinski A, Kobilka B K, Ziman B, et al. Culture and adenoviral infection of adult mouse cardiac myocytes: methods for cellular genetic physiology. *Am J Physiol Heart Circ Physiol.* 2000 July; 279(1): H429-36.
35. He H, Meyer M, Martin J L, McDonough P M, Ho P, Lou X, et al. Effects of mutant and antisense RNA of phospholamban on SR Ca(2+)-ATPase activity and cardiac myocyte contractility. *Circulation.* 1999 Aug. 31; 100(9): 974-80.
36. Luo W, Chu G, Sato Y, Zhou Z, Kadambi V J, Kranias E G. Transgenic approaches to define the functional role of dual site phospholamban phosphorylation. *J Biol Chem.* 1998 Feb. 20; 273(8): 4734-9.

What is claimed is:

1. A method for treating a disease associated with phospholamban (PLB) selected from the group consisting of heart failure, congestive heart failure, and ischemia, the method comprising administering to a subject in need thereof, (a) a pharmaceutically effective amount of a decoy peptide consisting of the peptide sequence represented by the following Formula I:

$$X_1\text{-Ala-}X_2\text{-}X_3\text{-Ile-Glu-}X_4 \qquad (1)$$

wherein $X_1$ represents 0-1 amino acid residue(s), $X_2$ represents Ser, Glu, or Asp, $X_3$ represents Thr, Glu, or Asp and $X_4$ represents 0-3 amino acid residue(s), with the proviso that $X_2$ is not Ser when $X_3$ is Thr;

wherein the decoy peptide inhibits protein phosphatase 1 (PP1)-mediated dephosphorylation of PLB by competitive inhibition, wherein neither $X_1$ nor $X_4$ comprise membrane-spanning domains and $X_1$ is not Tyr, and wherein the decoy peptide is linked to a cell membrane-permeable peptide;

and (b) a pharmaceutically acceptable carrier.

2. The method according to claim 1, wherein $X_1$ is Arg.

3. The method according to claim 1, wherein $X_4$ is Met, Met-Pro, or Met-Pro-Gln.

4. The method according to claim 1, wherein $X_2$ is Glu or Asp and $X_3$ is Thr, Glu, or Asp.

5. The method according to claim 1, wherein the decoy peptide consists of the amino acid sequence selected from the group of the amino acid sequences of SEQ ID NOs:1-6.

* * * * *